(12) United States Patent
Darian

(10) Patent No.: US 11,096,711 B2
(45) Date of Patent: Aug. 24, 2021

(54) ULTRASONIC SURGICAL APPARATUS AND ASSOCIATED METHOD

(71) Applicant: MISONIX, INC., Farmingdale, NY (US)

(72) Inventor: Alexander Darian, Brightwaters, NY (US)

(73) Assignee: MISONIX, INCORPORATED, Farmingdale, NY (US)

( * ) Notice: Subject to any disclaimer, the term of this patent is extended or adjusted under 35 U.S.C. 154(b) by 179 days.

(21) Appl. No.: 16/126,649

(22) Filed: Sep. 10, 2018

(65) Prior Publication Data

US 2019/0009071 A1 Jan. 10, 2019

Related U.S. Application Data

(62) Division of application No. 14/733,260, filed on Jun. 8, 2015, now Pat. No. 10,092,741.

(51) Int. Cl.
*A61B 17/32* (2006.01)
*A61B 17/00* (2006.01)
(Continued)

(52) U.S. Cl.
CPC ........ *A61B 17/320068* (2013.01); *A61B 5/24* (2021.01); *A61B 2017/00022* (2013.01);
(Continued)

(58) Field of Classification Search
CPC ........ A61B 5/04001; A61B 17/320068; A61B 2017/00022; A61B 2017/00039;
(Continued)

(56) References Cited

U.S. PATENT DOCUMENTS

| 2001/0003155 A1 | 6/2001 | Rockley et al. |
| 2003/0149368 A1 | 8/2003 | Hennemann ....... A61B 5/02007 600/483 |

(Continued)

FOREIGN PATENT DOCUMENTS

| CA | 1296067 C | 2/1992 |
| CN | 1525839 A | 9/2004 |

(Continued)

OTHER PUBLICATIONS

Ehab Shiban, MD, et al, "Continuous subcortical motor evoked potential stimulatio using the tip of an ultrasonic aspirator for the resection of motor eloquent lesions." Journal of Neurosurgery, May 15, 2015, pp. 1-6, Munich, Germany.

*Primary Examiner* — Jocelin C Tanner
(74) *Attorney, Agent, or Firm* — R. Neil Sudol; Henry D. Coleman

(57) ABSTRACT

A surgical instrument assembly has (i) a surgical instrument including a handpiece and a probe or horn attached to the handpiece, (ii) a source of ultrasonic vibratory energy operatively connected to the probe or horn, (iii) a source of electrical current operatively connected to deliver electrical current to organic tissues of a patient at a surgical site contacted by a distal end of the probe or horn, and (iv) a sensor of electrical potential disposable in contact with the patient at a desired distance from the surgical site. The sensor is operatively connected to the source of ultrasonic vibratory energy to automatically attenuate an output thereof in response to a detected potential of a predetermined magnitude.

12 Claims, 2 Drawing Sheets

(51) Int. Cl.
*A61B 90/00* (2016.01)
*A61B 5/24* (2021.01)

(52) U.S. Cl.
CPC ............... *A61B 2017/00039* (2013.01); *A61B 2017/00119* (2013.01); *A61B 2017/00761* (2013.01); *A61B 2017/32007* (2017.08); *A61B 2017/320069* (2017.08); *A61B 2017/320082* (2017.08); *A61B 2017/320084* (2013.01); *A61B 2017/320089* (2017.08); *A61B 2090/08021* (2016.02); *A61B 2217/005* (2013.01); *A61B 2505/05* (2013.01)

(58) Field of Classification Search
CPC ........... A61B 2017/00119; A61B 2017/00761; A61B 2017/320069; A61B 2017/32007; A61B 2017/320082; A61B 2017/320084; A61B 2017/320089; A61B 2090/08021; A61B 2217/005; A61B 2505/05
See application file for complete search history.

(56) References Cited

U.S. PATENT DOCUMENTS

| | | | | |
|---|---|---|---|---|
| 2007/0100378 | A1 | 5/2007 | Maschino | A61N 1/32 607/2 |
| 2007/0262879 | A1* | 11/2007 | Greiner | H04L 12/66 340/870.21 |
| 2008/0146921 | A1* | 6/2008 | Novak | A61B 17/320068 600/437 |
| 2008/0214967 | A1 | 9/2008 | Aranyi | A61B 17/320068 601/3 |
| 2008/0294044 | A1* | 11/2008 | Voic | A61B 17/320068 600/439 |
| 2010/0076366 | A1 | 3/2010 | Henderson, Sr. | A61B 5/031 604/9 |
| 2010/0185197 | A1* | 7/2010 | Sakao | A61B 18/1445 606/51 |
| 2012/0116433 | A1 | 5/2012 | Houser | A61B 17/00234 606/169 |
| 2013/0150751 | A1 | 6/2013 | Fiebig et al. | |
| 2013/0261368 | A1 | 10/2013 | Schwartz | A61N 5/1027 600/1 |
| 2014/0128863 | A1* | 5/2014 | Du | A61B 17/22012 606/34 |
| 2014/0276770 | A1* | 9/2014 | Ellman | A61B 18/1402 606/34 |
| 2015/0105791 | A1* | 4/2015 | Truckai | A61B 17/00234 606/115 |

FOREIGN PATENT DOCUMENTS

| | | |
|---|---|---|
| CN | 101495025 A | 7/2009 |
| CN | 101888813 A | 11/2010 |
| RU | 2255685 C2 | 7/2005 |
| WO | WO 1987/001276 A1 | 3/1997 |
| WO | WO 2013/154925 A2 | 10/2013 |

* cited by examiner

ULTRASONIC SURGICAL APPARATUS AND ASSOCIATED METHOD

CROSS-REFERENCE TO RELATED APPLICATION

This application is a division of application Ser. No. 14/733,260 filed Jun. 8, 2015, now U.S. Pat. No. 10,092,741, issued Oct. 9, 2018.

BACKGROUND OF THE INVENTION

This invention relates to surgical instruments and associated methods of use. More particularly, this invention relates to the use of ultrasound energy in surgical treatments. The invention contemplates method and apparatus for reducing undesirable tissue damage at an operative site. The invention may be used in neurosurgery and general surgery such as liver resection, or in the treatment of wounds, warts or other lesions, wrinkles or skin disease. Alternatively the invention may be used in laparoscopy.

Over the past 30 years, several ultrasonic tools have been invented which can be used to ablate or cut tissue in surgery. Such devices are disclosed by Wuchinich et al. in U.S. Pat. No. 4,223,676 and Idemoto et al in U.S. Pat. No. 5,188,102.

In practice, these surgical devices include a blunt tip hollow probe that vibrates at frequencies between 20 kc and 100 kc, with amplitudes up to 300 microns or more. Such devices ablate tissue by either producing cavitation bubbles which implode and disrupt cells, by generating tissue compression and relaxation stresses (sometimes called the jackhammer effect) or by other mechanisms such as micro streaming of bubbles in the tissue matrix. The effect is that the tissue becomes liquefied and separated. The fragmented tissue becomes emulsified with an irrigant solution. The resulting emulsion or slurry of tissue debris is then aspirated from the site. Bulk excision of tissue is possible by applying the energy around and under an unwanted tissue mass to separate it from the surrounding structure. The surgeon can then lift the separated tissue mass out using common tools such as forceps.

The tubular probe is excited by a vibratory energy source or transducer of either the piezoelectric or magnetostrictive type that transforms an alternating electrical signal within the frequencies indicated above into a longitudinal and/or transverse vibration. When the probe is attached to the transducer, the two become a single element with series and parallel resonances. The designer will try to tailor the mechanical and electrical characteristics of these elements to provide the proper frequency of operation. Most of the time, the elements will have a long straight axis and an operative tip truncated in a plane perpendicular to the long axis. This is done for simplicity and economic considerations. In almost all applications, whether medical or industrial, such an embodiment is practical and useful.

Therefore, it was desired to provide a probe that can be mated to an ultrasonic surgical aspirator that increases the efficiency of emulsification, does not heat up the operative site and lowers the time of operation.

Ultrasonic ablation tools need to be driven at high excursion levels, i.e., high vibrational amplitudes in order to effectively remove unwanted tissue. Once this tissue is removed, the high amplitudes can lead to higher pain perception on the part of the patient and can also lead to destruction of viable tissue such as nerve tissue if the operator is not careful.

OBJECTS OF THE INVENTION

An object of the present invention is to provide an improved ultrasonic surgical instrument.

A more specific object of the present invention is to provide an improved ultrasonic surgical instrument for use in the removal of soft and hard organic tissue adjacent to critical anatomical structures such as blood vessels and nerves.

Accordingly, it is an object of the present invention is to provide an improved ultrasonic surgical instrument that enhances surgical efficiency and reduces the likelihood of damage to one or more specific organs of the patient, for instance, nerve tissue or blood vessels.

A related object of the present invention is to provide an ultrasonic treatment method which reduces the chances of damage to nerves and/or blood vessels.

These and other objects of the invention will be apparent from the drawings and descriptions herein. Although every object of the invention is attained in at least one embodiment of the invention, there is not necessarily any embodiment which attains all of the objects of the invention.

SUMMARY OF THE INVENTION

A surgical instrument assembly in accordance with the present invention comprises (i) a surgical instrument including a handpiece and a probe or horn attached to the handpiece, (ii) a source of ultrasonic vibratory energy operatively connected to the probe or horn, (iii) a source of electrical current operatively connected to deliver electrical current to organic tissues of a patient at a surgical site contacted by a distal end of the probe or horn, and (iv) a sensor of electrical potential disposable in contact with the patient at a desired distance from the surgical site. The sensor is operatively connected to the source of ultrasonic vibratory energy to automatically attenuate an output thereof in response to a detected potential of a predetermined magnitude.

In a related embodiment of the present invention, instead of being connected to the source of ultrasonic vibratory energy, the sensor may be operatively connected to an alert signal generator such as an electroacoustic transducer or light source that automatically delivers a warning to the operating surgeon for purposes of enabling the surgeon to take effective action, such as moving the instrument away from the sensitive tissues and/or reducing the magnitude of applied energy.

The sensor may take the form of an electrode adapted for placement on a tissue surface of the patient proximate to a nerve or nerve bundle of the patient. Alternatively, the sensor may be an electrode configured for placement in or on a blood vessel. In either case, the electrode functions as a proximity sensor indicating that the ultrasonic action is occurring close to easily damaged tissue such as nerves or blood vessels.

The attenuation of the ultrasonic vibratory energy may be variable in accordance with the magnitude of the electrical potential as detected by the sensor. The greater the potential, the more likely that continued application of ultrasonic energy might damage the tissue being monitored. Accordingly, the greater the sensed potential, the more the ultrasound energy is attenuated. The ultrasonic vibratory energy may be reduced until the magnitude of the detected potential falls to a predetermined acceptable upper limit. In the case that a nerve or nerve bundle is being monitored by the sensor, the sensed potential may be a maximum amplitude of nerve activation or alternatively may be an average potential computed over several cycles of nerve activation.

Pursuant to another feature of the present invention, the predetermined threshold for initiating reduction in ultrasonic energy application to the surgical site may be modifiable by the surgeon or operator. Thus, the instrument assembly may be provided with at least one operator-adjustable input element operatively connected to the source of ultrasonic vibratory energy to vary a degree of attenuation of the output in accordance with a magnitude of potential detected by the sensor.

Typically, an ultrasonic instrument assembly may, include irrigation and aspiration to remove fragmented organic tissues from the surgical site. Inasmuch as the aspiration may cause damage to delicate nerve tissue or blood vessels, the sensor may be operatively connected to a source of vacuum underpressure to automatically attenuate an output level thereof in response to a detected potential of a predetermined magnitude.

Accordingly, a surgical instrument assembly in accordance with the present invention comprises (i) a surgical instrument including a handpiece and a probe or horn attached to the handpiece, (ii) a first source of ultrasonic vibratory energy operatively connected to the probe or horn, (iii) a second source of electrical current operatively connected to the instrument to deliver electrical current to organic tissues of a patient at a surgical site contacted by a distal end of the probe or horn, (iv) a third source of vacuum underpressure connected to the instrument to apply suction to the surgical site via the instrument, and (v) a sensor of electrical potential disposable in contact with the patient at a desired distance from the surgical site. The sensor is operatively connected to at least the first source or the third source to automatically attenuate an output thereof in response to a detected potential of a predetermined magnitude.

The instrument assembly may be configured to have either the ultrasound or the suction, or both, attenuated in response to a detection of a threshold magnitude of electrical potential along a nerve path or along a blood vessel. The threshold potential and the degree or proportion of power attenuation may differ between the two modalities, ultrasound and suction. Thus, attenuation or power reduction may be initiated at a lower level for one modality than the other. In addition, the rate or amount of attenuation or power reduction may be greater for one than the other.

A surgical method in accordance with the present invention comprises (a) providing a surgical instrument including a handpiece and a probe or horn attached to the handpiece, (b) placing a distal end or operative tip of the probe or horn in contact with organic tissues of a patient at an operative site, (c) disposing a sensor on the patient at a distance from the surgical site, (d) vibrating the probe or horn at an ultrasonic frequency during the contacting of the organic tissues with the distal end or operative tip, (e) conducting electrical current into the patient at least proximate the surgical site during the contacting of the organic tissues with the distal end or operative tip and the vibrating of the probe or horn, (f) operating the sensor to detect electrical potential during the contacting of the organic tissues with the distal end or operative tip and the vibrating of the probe or horn, and (g) attenuating the vibrating of the probe or horn in response to a detected potential of a predetermined magnitude.

The attenuating of the output may include operating a feedback loop to automatically attenuate at least one of the vibrating of the probe or horn and the degree of applied suction.

The attenuating of the output is optionally variable in accordance with a magnitude of potential detected by the sensor.

A surgical method in accordance with the present invention alternatively or additionally comprises (a) providing a surgical instrument including a handpiece and a probe or horn attached to the handpiece, (b) placing a distal end or operative tip of the probe or horn in contact with organic tissues of a patient at an operative site, (c) disposing a sensor on the patient at a distance from the surgical site, (d) vibrating the probe or horn at an ultrasonic frequency during the contacting of the organic tissues with the distal end or operative tip, (e) conducting electrical current into the patient at least proximate the surgical site during the contacting of the organic tissues with the distal end or operative tip and the vibrating of the probe or horn, (f) applying suction to the surgical site via the instrument during the contacting of the organic tissues with the distal end or operative tip and the vibrating of the probe or horn, (g) operating the sensor to detect electrical potential during the contacting of the organic tissues with the distal end or operative tip and the vibrating of the probe or horn, and (h) attenuating at least one of the vibrating of the probe or horn and the degree of applied suction in response to a detected potential of a predetermined magnitude.

Again, the attenuating of the output may include operating a feedback loop to automatically attenuate at least one of the vibrating of the probe or horn and the degree of applied suction. Also, the attenuating of the output may be variable in accordance with a magnitude of potential detected by the sensor.

The disposing of the sensor may include placing the sensor in operative contact with a tissue surface of the patient proximate to a nerve of the patient or placing the sensor in or in proximity to a blood vessel.

The method may further comprise adjusting an input element operatively connected to the instrument to vary a degree of the attenuating in accordance with a magnitude of potential detected by the sensor.

It is contemplated that the present invention may find wider application in surgery in general. Accordingly, a surgical instrument assembly in accordance with the present invention comprises a surgical instrument, a source of electrical current operatively connected to deliver electrical current to organic tissues of a patient at a surgical site contacted by a distal end of the instrument, and a sensor of electrical potential disposable in contact with the patient at a desired distance from the surgical site, the sensor being operatively connected to the instrument to automatically attenuate an output thereof in response to a detected potential of a predetermined magnitude. Where the instrument applies energy to organic tissues, such as ultrasound energy, electromagnetic radiation (e.g., infrared, optical, ultraviolet, etc., or a laser), or electrical current, attenuation may result from decreasing the magnitude or intensity of the applied energy. Alternatively, where the instrument is under robotic control, the attenuation may be effectuated in whole or in part by automatically moving the instrument away from the surgical site. As indicated above, the sensor may be alternatively or additionally connected to an alert signal generator for producing a warning signal in response to a detected potential of a predetermined magnitude. The attenuation of the applied energy is then undertaken by the operator in response to the alert or warning signal.

DETAILED DESCRIPTION

Figure 1:
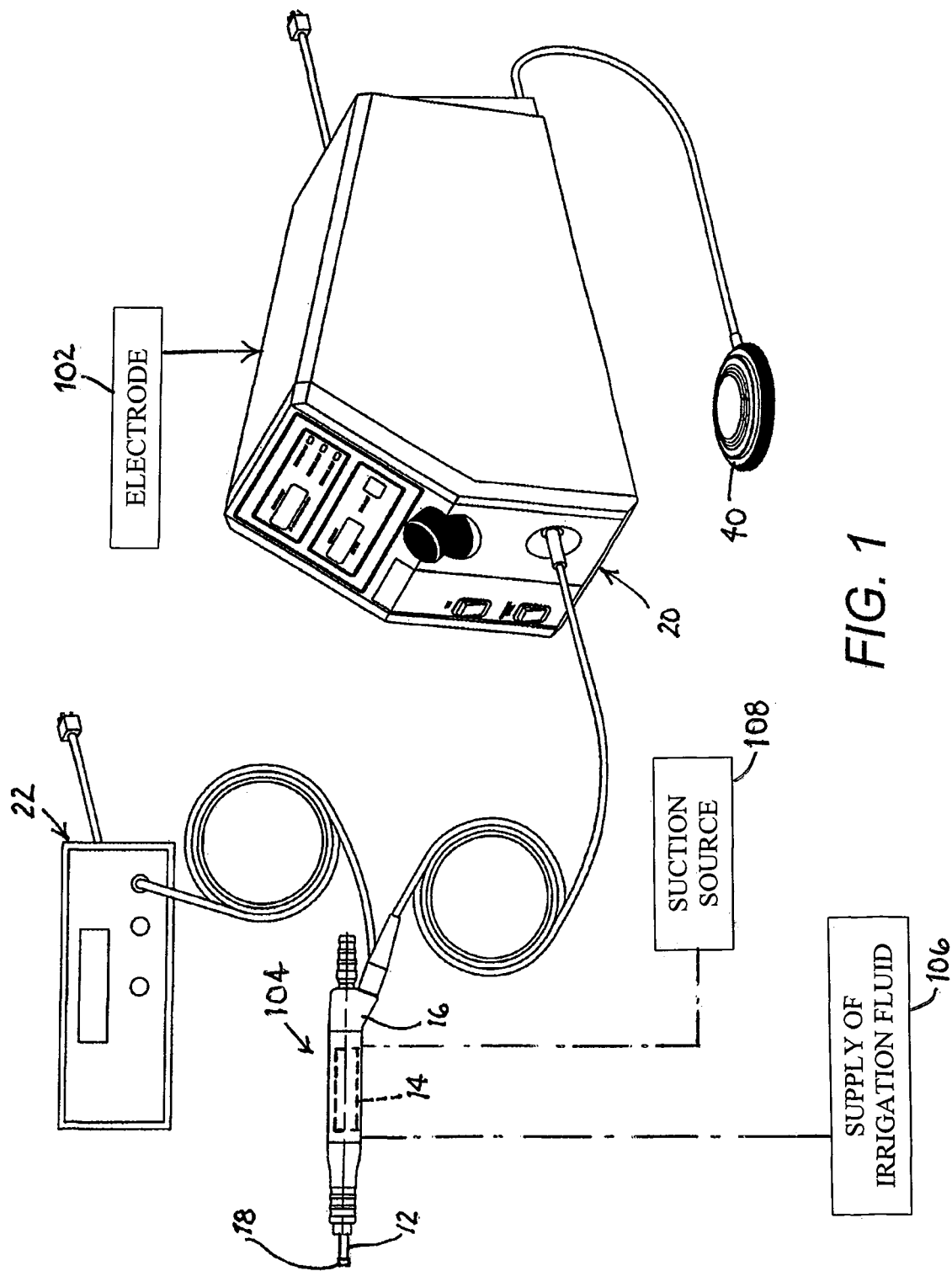
FIG. 1 is partially a schematic perspective vie and partially an elevational view of a medical treatment assembly or system in accordance with the present invention.

As depicted in FIG. 1, a medical treatment or surgical assembly comprises an ultrasonic instrument 104 including a probe 12 operatively connected to a transducer assembly 14 in a handpiece 16 for receiving therefrom mechanical vibratory energy so that an operative tip 18 of the probe oscillates at an ultrasonic frequency suitable for performing a surgical procedure such as wound abrasion or other removal of organic tissues. A first electrical voltage source or generator 20 is operatively connected to transducer assembly 14 for energizing the assembly with an alternating voltage having an ultrasonic frequency. A second electrical voltage source or generator 22 is operatively connected to probe 12 for feeding thereto a signal of limited current and limited voltage to be conducted into a patient through the operative tip 18 of the probe (or other metal part such a sheath or an electrode on the sheath) after placement of the operative tip into contact with the patient. The signal produced by source 22 has a current and a voltage (or power output) so limited as to prevent damage to organic tissues of the patient while enabling detection of a resulting electrical potential or current in tissues of the patient at a distance from an operative or surgical site to which distal end or operative tip 18 of probe 12 is applied. The detection is effectuated by means of an electrode sensor 102 adapted for attachment exemplarily to a skin surface of the patient over a nerve fiber or bundle proximate a target surgical site or, alternatively, for disposition in or near a blood vessel proximate the surgical site.

The current and voltage parameters or the electrical signal produced by voltage source or generator 22 are substantially the same as those of known devices for intraoperative neurophysiological monitoring (IONM) or intraoperative neuromonitoring where electrophysiological methods such as electroencephalography (EEG), electromyography (EMG), and evoked potentials are used to monitor the functional integrity of certain neural structures (e.g., nerves, spinal cord and parts of the brain) during surgery. The purpose of IONM is to reduce the risk to the patient of iatrogenic damage to the nervous system, and/or to provide functional guidance to the surgeon and anesthesiologist.

As further depicted in FIG. 1, the medical treatment or surgical assembly additionally includes an irrigation fluid supply 106 and a suction source or vacuum generator 108 connected to instrument 104 respectively for supplying a fluid irrigant such as saline solution to a surgical site and for aspirating a slurry of tissue fragments from the surgical site.

Figure 2:
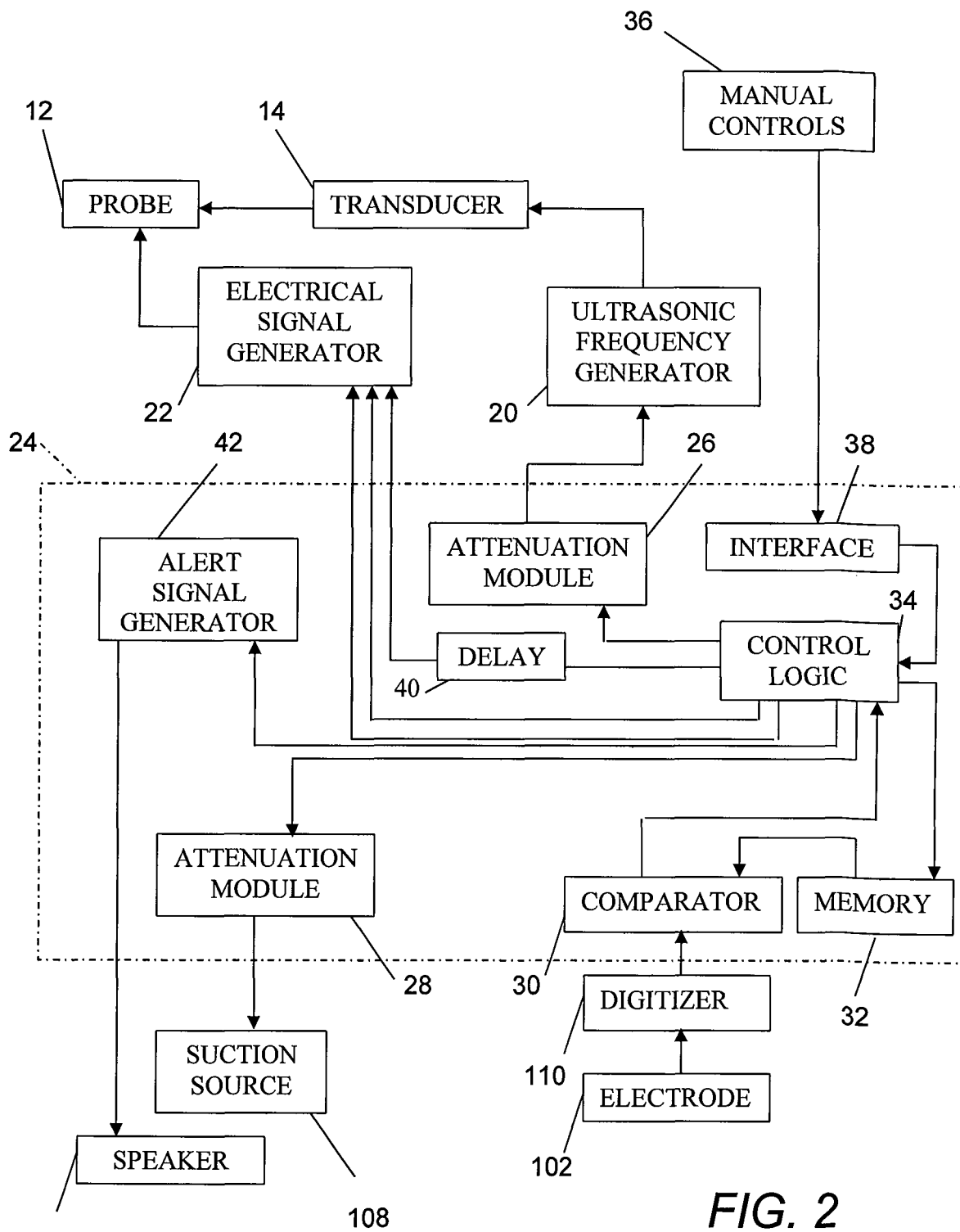
FIG. 2 is a block diagram of functional components of the device or system of FIG. 1.

As shown in FIG. 2, the medical treatment assembly further comprises a control unit or circuit 24 operatively connected to voltage sources 20 and 22 in part for synchronizing the conducting of the electrical monitoring signal into the patient via instrument 104 with the vibrating of probe 12. Typically, an electrical current from source 22 is conducted through probe 12 and operative tip 18 thereof only when the probe is vibrating under the action of transducer 14 when energized by an ultrasonic waveform of predetermined frequency from generator or source 20. Control circuit 24 is also connected to suction source or vacuum generator 108, as well as to ultrasonic frequency generator or voltage source 20, for attenuating or reducing the magnitude of applied suction and/or ultrasonic vibratory energy upon a detection via electrode or sensor 102 of an increase in electrical potential at the site of the electrode indicating such proximity of operative tip 18 to a nerve or blood vessel as to possibly result in damage to the nerve or blood vessel, should the suction or ultrasonic vibratory energy continue unabated. More specifically, control circuit 24 includes a first power adjustment module 26 operatively connected to voltage source 20 for selectively attenuating or reducing the amplitude of the ultrasonic waveform output thereof. A second power adjustment module 28 is operatively connected to suction source 108 for selectively attenuating or reducing the amount of suction or magnitude of vacuum pressure generated thereby and communicated to instrument 104.

Electrode or sensor 102 is connected to control unit 24 via a digitizer or analog-to-digital converter 110. Control unit 24 includes a comparator 30 that receives an encoded electrical-potential magnitude from converter 110 and compares the magnitude with a predetermined reference or threshold stored in a memory 32. The result of the comparison is fed to a control logic circuit 34 having outputs connected to power adjustment modules 26 and 28 for triggering or modulating the operation thereof.

Control logic 34 receives operator instructions from manual controls 36 via an interface 38. In response to operator instructions, control logic 34 may modify the reference or threshold value stored in memory 32. Memory 32 may optionally store a plurality of reference values. For instance, a lower reference or threshold may be used for triggering or initiating an increase in power output of either ultrasonic frequency generator 20 or suction source 108. Upper and lower thresholds may be set for defining a range of applied power for ultrasonic frequency generator 20 and/or suction source 108. In addition, separate thresholds may be defined for ultrasonic vibratory energy and suction. In another embodiment or modification, multiple electrodes or sensors 102 may be provided. The different sensors 102 may be disposed at different locations on or in a patient proximate a surgical site and may monitor electrical potentials of different nerves and/or different blood vessels. The output signals of the different electrode sensors 102 may be multiplexed, i.e., monitored in respective time segments, and processed sequentially or in seriatim by comparator 30. Alternatively, multiple comparators 30 may be provided for parallel signal processing.

Control unit 24 may include a time delay element 40 for enabling a commencing of probe vibration only after a predetermined time period has elapsed after a conducting of the electrical signal into the patient has commenced. Thus, in the event that the operative tip 18 of the instrument 104 is initially placed too close to sensitive tissue, there is an opportunity for control logic 34 to temporarily block or modulate the operation of the ultrasonic and/or suction modality. Delay element 40 may be incorporated into control logic 34 or power adjustment circuit 26.

The reaching of a threshold, the adjustment in power output of ultrasonic waveform generator 20 or suction source 108 may be communicated to the operator by an alert signal generator 42 which activates an electroacoustic transducer or speaker 44 in response to a signal from control logic 34.

In using the treatment apparatus of FIGS. 1 and 2, sensor electrode 102 is placed on the patient at a distance from the contemplated surgical site. A surgeon manipulates handpiece 16 to place probe tip 18 into contact with a patient at a surgical site. Voltage source 22 is operated to generate the proximity-detection electrical voltage or potential, which is conducted into the patient through probe tip 18 while the probe tip is in contact with the patient. Either simultaneously with or subsequently to the commencement of current conduction, source 20 is activated to energize transducer assembly 14 for generating, in probe 12, a standing mechanical compression wave having an ultrasonic frequency. Operative tip 18, typically located at an anti-node of the standing compression wave, vibrates at the ultrasonic frequency.

Sensor electrode 102 is operated to detect electrical potential during the contacting of the organic tissues with distal instrument end or operative tip 18 and the vibrating of probe or horn 12. In response to signals from comparator 30 indicative of a breach of a proximity threshold, control logic 34 and power adjustment module 26 act to selectively attenuate or reducing the amplitude of the ultrasonic waveform output of voltage source or waveform generator 20. Voltage source 22, electrode 102, comparator 30, control logic 34 and power adjustment module 26 function as a feedback loop to modulate or limit the vibrating of probe or horn 12 in accordance with the electrical potential detected by sensor electrode 102, thereby preventing or minimizing damage to nerves or blood vessels owing to ultrasonically induced heat, cavitation or other impact on organic tissues.

Additionally or alternatively, where suction source 108 is provided and utilized to aspirate tissue fragments from the surgical site, a feedback loop including control logic 34 and power adjustment module 28 may be operated to induce suction source 108 to automatically attenuate the degree of applied suction to prevent or minimize damage to nerves or blood vessels owing to vacuum forces.

Attenuating the output of ultrasonic waveform generator 20 or suction source 108 is optionally variable in accordance with a magnitude of potential detected by the sensor. Accordingly, an operator may provide instructions to control logic 34 via manual controls 36 and interface 38 to modify the reference or threshold value(s) stored in memory 32.

Although the invention has been described in terms of particular embodiments and applications, one of ordinary skill in the art, in light of this teaching, can generate additional embodiments and modifications without departing from the spirit of or exceeding the scope of the claimed invention. For instance, automatic attenuation of output energy may be omitted in favor of alert signal generator 42. In that case, the operator or surgeon is responsible for moderating undesirable effects on sensitive organic tissues, for instance, by removing the probe 12 from the operative site or reducing output energy. Also, alert signal generator 42 may take a form other than electroacoustic, for instance, electro-optical or electrochemical (e.g., an atomizer spraying a mist of fragrant composition). In addition, probe 12 may take the form of a general purpose surgical tool, e.g., a scalpel, a cauterizer, or an aspirator, provided at a tissue-contacting surface with an electrode carrying current from signal generator 22. Where probe 12 is an aspirator or suction cannula, the sensor 102 is operatively connected solely to suction source 108 for purpose of protecting sensitive tissues.

Accordingly, it is to be understood that the drawings and descriptions herein are proffered by way of example to facilitate comprehension of the invention and should not be construed to limit the scope thereof.

What is claimed is:

1. A surgical instrument assembly comprising:
   a surgical instrument including a handpiece and a probe or horn attached to said handpiece;
   a source of ultrasonic vibratory energy operatively connected to said probe or horn;
   a source of electrical current operatively connected to said probe or horn to deliver electrical current, to organic tissues of a patient at a surgical site contacted by a distal end of said probe or horn, in an amount so limited as to prevent damage to any organic tissues of the patient including the organic tissues at the surgical site; and
   a sensor of electrical potential configured for contact with the patient at a desired location spaced from the surgical site and said instrument and disposable independently of said instrument,
   said sensor and said source of ultrasonic vibratory energy being operatively connected to one another in a configuration to automatically attenuate an output of said source of ultrasonic vibratory energy in response to a potential of a predetermined magnitude detected by said sensor.

2. The instrument assembly defined in claim 1 wherein the attenuation of said output is variable in accordance with a magnitude of potential detected by said sensor.

3. The instrument assembly defined in claim 1 wherein said sensor is an electrode adapted for placement on a tissue surface of the patient proximate to a nerve of the patient.

4. The instrument assembly defined in claim 1 wherein said sensor is an electrode configured for placement in a blood vessel.

5. The instrument assembly defined in claim 1, further comprising at least one operator-adjustable input element operatively connected to said source of ultrasonic vibratory energy to vary a degree of attenuation of said output in accordance with a magnitude of potential detected by said sensor.

6. The instrument assembly defined in claim 1, further comprising a source of vacuum underpressure connected to said instrument to apply suction to said surgical site via said instrument, said sensor being operatively connected to said source of vacuum underpressure to automatically attenuate an output level thereof in response to a detected potential of a predetermined magnitude.

7. The instrument assembly defined in claim 6 wherein the attenuation of said output level is variable in accordance with a magnitude of potential detected by said sensor.

8. A surgical instrument assembly comprising:
   a surgical instrument including a handpiece and a probe or horn attached to said handpiece;
   a first source of ultrasonic vibratory energy operatively connected to said probe or horn;
   a second source of electrical current operatively connected to said instrument to deliver electrical current, to organic tissues of a patient at a surgical site contacted by a distal end of said probe or horn, in an amount so limited as to prevent damage to any organic tissues of the patient including the organic tissues at the surgical site;
   a third source of vacuum underpressure connected to said instrument to apply suction to said surgical site via said instrument; and a sensor of electrical potential configured for contact with the patient at a desired location spaced from the surgical site and said instrument and disposable independently of said instrument, said sensor, said first source and said third source being operatively connected to one another in a configuration to automatically attenuate an output of at least one of said first source and said third source in response to a potential of a predetermined magnitude detected by said sensor.

9. The instrument assembly defined in claim 8 wherein the attenuation of said output is variable in accordance with a magnitude of potential detected by said sensor.

10. The instrument assembly defined in claim 8 wherein said sensor is an electrode adapted for placement on a tissue surface of the patient proximate to a nerve of the patient.

11. The instrument assembly defined in claim 8 wherein said sensor is an electrode configured for placement in a blood vessel.

12. The instrument assembly defined in claim 8, further comprising at least one operator adjustable input element operatively connected to said at least one of said first source and said third source to vary a degree of attenuation of said output in accordance with a magnitude of potential detected by said sensor.

* * * * *